(12) United States Patent
Tang et al.

(10) Patent No.: US 11,607,686 B2
(45) Date of Patent: Mar. 21, 2023

(54) SAMPLE COLLECTING DEVICE

(71) Applicant: Ovation Health Science and Technology Co., Ltd, Langfang (CN)

(72) Inventors: Bruce Qing Tang, Langfang (CN); Chen Steven Song, Langfang (CN); Changqing Liu, Langfang (CN); Yuzhu Yao, Langfang (CN); Xihu Yu, Langfang (CN); Feiteng Liu, Langfang (CN); Ke Liu, Langfang (CN); Weilong Wu, Langfang (CN)

(73) Assignee: OVATION HEALTH SCIENCE AND TECHNOLOGY CO., LTD, Langfang (CN)

( * ) Notice: Subject to any disclaimer, the term of this patent is extended or adjusted under 35 U.S.C. 154(b) by 148 days.

(21) Appl. No.: 17/168,652

(22) Filed: Feb. 5, 2021

(65) Prior Publication Data
US 2022/0184615 A1   Jun. 16, 2022

(30) Foreign Application Priority Data

Dec. 14, 2020   (CN) .......................... 202011471653.X (51) Int. Cl.
*B01L 3/00* (2006.01)
*A61B 10/00* (2006.01)

(52) U.S. Cl.
CPC .... *B01L 3/502715* (2013.01); *A61B 10/0038* (2013.01); *A61B 10/0096* (2013.01); *B01L 2200/0689* (2013.01); *B01L 2200/16* (2013.01); *B01L 2300/0609* (2013.01); *B01L 2300/0681* (2013.01); *B01L 2300/087* (2013.01); *B01L 2400/0644* (2013.01); *B01L 2400/0683* (2013.01)

(58) Field of Classification Search
CPC ....... B01L 3/502715; B01L 2200/0689; B01L 2200/16; B01L 2300/0609; B01L 2300/0681; B01L 2300/087; B01L 2400/0644; B01L 2400/0683; A61B 10/0038; A61B 10/0096
See application file for complete search history.

(56) References Cited

U.S. PATENT DOCUMENTS

| 4,981,144 A * | 1/1991 | Carels, Jr. ................ A61B 5/20 141/237 |
| 2002/0106814 A1* | 8/2002 | Matsubara ....... G01N 35/00603 422/67 |
| 2016/0031088 A1* | 2/2016 | Suzuki .................... B25J 9/026 414/222.08 |

* cited by examiner

*Primary Examiner* — Matthew D Krcha
*Assistant Examiner* — Tingchen Shi
(74) *Attorney, Agent, or Firm* — WPAT, PC (57) ABSTRACT

A sample collecting device is provided. The sample collecting device includes a frame, a collect part and a control part. The collect part is disposed in the frame and is provided with a collecting cavity having a collecting port, and the collect part is used to make a sample flow into the collecting cavity from the collecting port. The control part is disposed in the frame, used to make a collecting rod put into a reagent bottle be pulled out and inserted into the collecting cavity to thereby collect the sample, and used to make the collecting rod with the sample be pulled out from the collecting cavity and put back into the reagent bottle. The collecting of sample without manual intervention is realized, effectiveness and consistency of the collected samples are ensured, and the labor cost is reduced.

9 Claims, 6 Drawing Sheets

SAMPLE COLLECTING DEVICE

TECHNICAL FIELD

The disclosure relates to the field of sample collecting technology, and more particularly to a sample collecting device.

DESCRIPTION OF RELATED ART

With the pace of modern life getting faster and faster, the living environment getting worse and worse, and the working pressure increasing, people's physical condition is deteriorating. In this case, people are paying more and more attention to their own physical health. It is cumbersome to go to a hospital or health room to register, queue, and obtain results to check their physical conditions. Therefore, personal health products tailored for individuals come into being. Judging a physical condition of feces is an important indicator. At present, most of the feces collection on the market is manual collection. However the collecting process is unhygienic and sometimes the collected sample does not meet inspection standards.

SUMMARY

A sample collection device provided in this disclosure can automatically collect feces samples without manual intervention.

One aspect, a sample collecting device provided in an embodiment of the disclosure includes: a frame; a collect part, disposed in the frame, wherein the collect part is provided with a collecting cavity having a collecting port, and the collect part is configured to make a sample flow into the collecting cavity from the collecting port; and a control part, disposed in the frame, wherein the control part is configured to make a collecting rod put into a reagent bottle be pulled out of the reagent bottle and inserted into the collecting cavity to collect the sample, and configured to make the collecting rod with the sample be pulled out from the collecting cavity and put back into the reagent bottle.

In an embodiment of the disclosure, the collecting port is located on a top wall of the collecting cavity, a discharge outlet is provided on a bottom wall of the collecting cavity, and an insertion port is provided on a side wall of the collecting cavity, so that the sample is capable of flowing into the collecting cavity from the collecting port and then discharging from the discharge outlet, and the collecting rod is capable of being inserted into the collecting cavity from the insertion port.

In an embodiment of the disclosure, the side wall of the collecting cavity is gradually tapered downward, so that the sample flowing in from the collecting port converges towards and discharges from the discharge outlet.

In an embodiment of the disclosure, a periphery of the insertion port is surrounded by a guide wall outwardly protruding from the collecting cavity, and a side wall of the guide wall gradually expands along a direction away from the collecting cavity, so that the collecting rod is capable of being inserted into the collecting cavity from the insertion port under the guiding of the guide wall.

In an embodiment of the disclosure, the sample collecting device further includes a water supply pipe, wherein the water supply pipe is disposed on the frame, the water supply pipe is formed with a water supply channel having a water inlet and a water outlet, the water inlet is connected with an external water source, and the water outlet is arranged opposite to the collecting port in a vertical direction so as to supply a water to flush an inner wall of the collecting cavity.

In an embodiment of the disclosure, the sample collecting device further includes a receiving box, wherein the receiving box is disposed in the frame, the receiving box is provided with a receiving tank having a receiving port, and the receiving port is arranged opposite to the discharge outlet in a vertical direction so as to a water flows into the receiving tank after flushing an inner wall of the collecting cavity.

In an embodiment of the disclosure, the control part includes: a first holder, configured to clamp and fix the reagent bottle, in which the collecting rod is put, in a state of an opening of the reagent bottle being upward; a first driver, connected with the first holder, wherein the first driver is configured to drive the first holder to move in a vertical direction; a second holder, disposed above the first holder, wherein the second holder is configured to clamp and fix the collecting rod put into the reagent bottle; a rotator, connected with the second holder, wherein the rotator is configured to rotate the second holder to make an axis of the collecting rod fixed by the second holder coincide with an axis of the insertion port and the collecting rod fixed by the second holder be vertically arranged; and a second driver, connected with the rotator, wherein the second driver is configured to drive the rotator to move along an axial direction of the insertion port.

In an embodiment of the disclosure, the first holder comprises a first fixing seat, a first positioning piece, a first clamping member and a first motor; the first positioning piece, the first clamping member and the first motor are individually disposed on the first fixing seat, the first clamping member is connected with the first motor by a first gear set and thereby the first clamping member rotates under the driving of the first motor and then cooperates with the first positioning piece to clamp the reagent bottle; the second holder comprises a second fixing seat, a second positioning piece, a second clamping member and a second motor; the second positioning piece, the second clamping member and the second motor are individually disposed on the second fixing seat, the second clamping member is connected with the second motor by a second gear set and thereby the second clamping member rotates under the driving of the second motor and then cooperates with the second positioning piece to clamp the collecting rod.

In an embodiment of the disclosure, the first driver comprises a first bracket, a first rack, a first driving motor and a first driving gear; the first rack, the first driving gear and the first driving motor are individually disposed on the first bracket; the first rack is arranged along the vertical direction, the first rack is connected with the first driving motor through the first gear set, the first rack is connected with the first holder, so that the first rack is driven to move in the vertical direction by the first driving motor and thereby drives the first holder to move in the vertical direction; the second driver comprises a second bracket, a second rack, a second driving motor and a second driving gear; the second rack, the second driving gear and the second driving motor are individually disposed on the second bracket; the second rack is arranged along the axial direction of the insertion port, the second rack is connected with the second driving motor through the second driving gear, and the second rack is connected with the rotator, so that the second rack is driven to move along the axial direction of the insertion port by the second driving motor and thereby drives the rotator to move in the axial direction of the insertion port.

In an embodiment of the disclosure, the rotator comprises a base, a connecting piece and a rotating motor; the connecting piece and the rotating motor are individually disposed on the base, the connecting piece is connected with the rotating motor through a rotating gear set, the connecting piece is connected with the second holder, and the base is connected with the second driver, so that the connecting piece is driven to rotate by the rotating motor and thereby drives the second holder to rotate.

A sample collecting device is provided according to embodiments of this disclosure. The sample collecting device includes a frame, a collect part and a control part. The collect part is disposed in the frame and is provided with a collecting cavity having a collecting port, and the collect part is used to make a sample flow into the collecting cavity from the collecting port. The control part is disposed in the frame, used to make a collecting rod put into a reagent bottle be pulled out of the reagent bottle and inserted into the collecting cavity to thereby collect the sample, and used to make the collecting rod with the sample be pulled out from the collecting cavity and put back into the reagent bottle. The disclosure realizes the sample collecting without manual intervention, ensures the effectiveness and consistency of the collected samples, and reduces labor cost.

BRIEF DESCRIPTION OF THE DRAWINGS

In order to more clearly illustrate technical solutions of embodiments of the disclosure, drawings used in the description of the embodiments will be briefly described below. Apparently, the drawings described below are merely some embodiments of the disclosure, and those skilled in the art can obtain other drawings based on these drawings without creative efforts.

DETAILED DESCRIPTION OF EMBODIMENTS

In order to make a purpose, technical solutions and advantages of the disclosure more clear, the embodiments of the disclosure will be clearly and completely described below, with reference to the accompanying drawings in the embodiments of the disclosure. It should be understood that, the described embodiments are merely some of the embodiments of the disclosure to explain the disclosure and are not used to limit the disclosure.

Referring to FIG. 1-7, the embodiments of the disclosure provides a sample collecting device 1. The sample collecting device 1 is particularly adapted for collecting feces sample. The sample collecting device 1 may be used as hospital diagnostic equipment, and can also be used at home.

Figure 1:
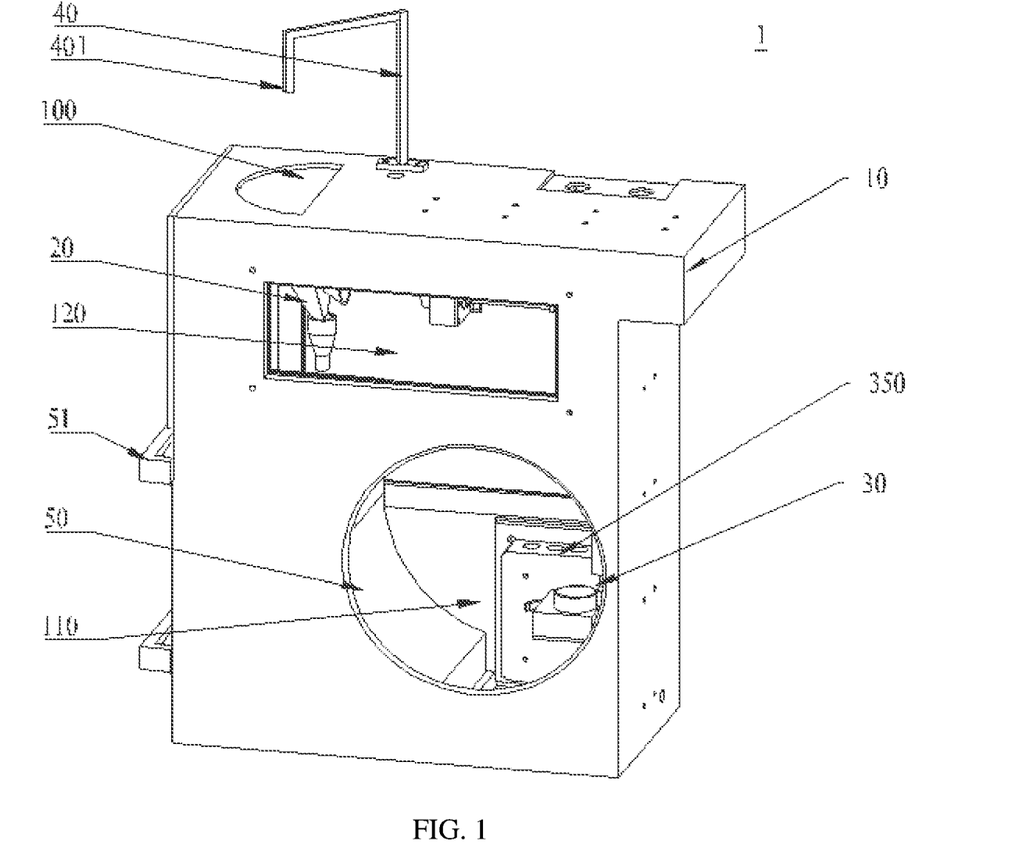
FIG. 1 is a first schematic structural view of a sample collecting device according to an embodiment of the disclosure.
Figure 2:
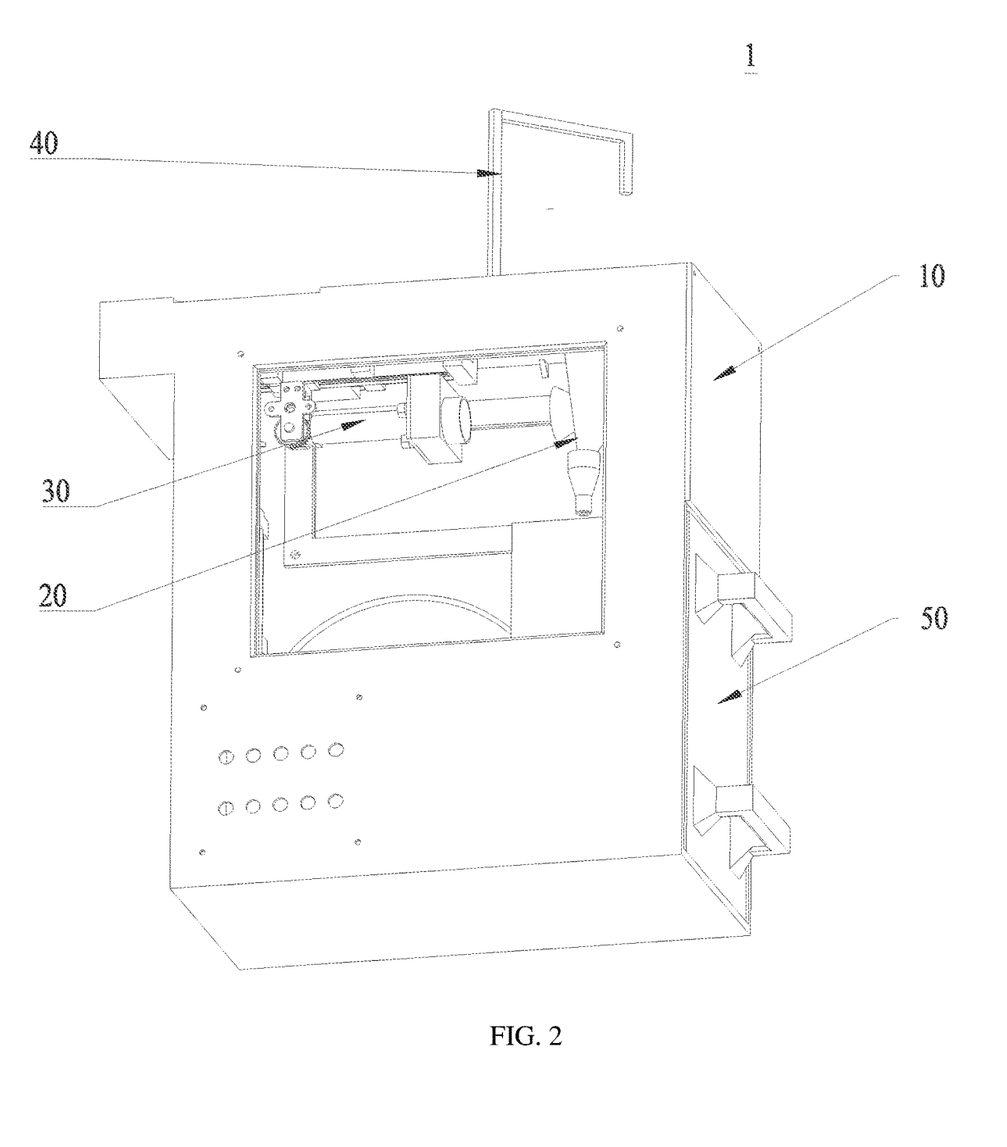
FIG. 2 is a second schematic structural view of a sample collecting device according to an embodiment of the disclosure.

The sample collecting device 1 includes a frame 10, a collect part 20 and a control part 30. The frame 10 is used to support the other parts of the sample collecting device 1. The frame 10 may be composed of a top plate, a bottom plate, a left side plate, a front plate, a right side plate and a rear plate. Thereby, the frame 10 defines an accommodation chamber.

The collect part 20 is used for collecting samples. The collect part 20 is provided with a collecting cavity 200 having a collecting port 210. The collect part 20 is configured to make the sample flow into the collecting cavity 200 from the collecting port 210. The collecting port 210 may be located on a top wall 201 of the collecting cavity 200. An axis of the collecting port 210 may extend in a vertical direction. A bottom wall 202 of the collecting cavity 200 may be provided with a discharge outlet 220. An axis of the discharge outlet 220 may extend in the vertical direction. A diameter of the collecting port 210 may be larger than that of the discharge outlet 220. Then, the sample flows into the collecting cavity 200 from the collecting port 210 and then discharges from the discharge outlet 220. A side wall 203 of the collecting cavity 200 is gradually tapered downward, so that the sample flowing in from the collecting port 210 converges towards and discharges from the discharge outlet 220. The collect part 20 is funnel-shaped. An insertion port 230 is provided on a side wall of the collecting cavity 200. An axis (as denoted by the dashed line in FIG. 3) of the insertion port 230 may extend horizontally. A periphery of the insertion port 230 may be surrounded by a guide wall 240 outwardly protruding from the collecting cavity 200, and a side wall of the guide wall 240 gradually expands along a direction away from the collecting cavity 200. The guide wall 240 is funnel-shaped.

Figure 3:
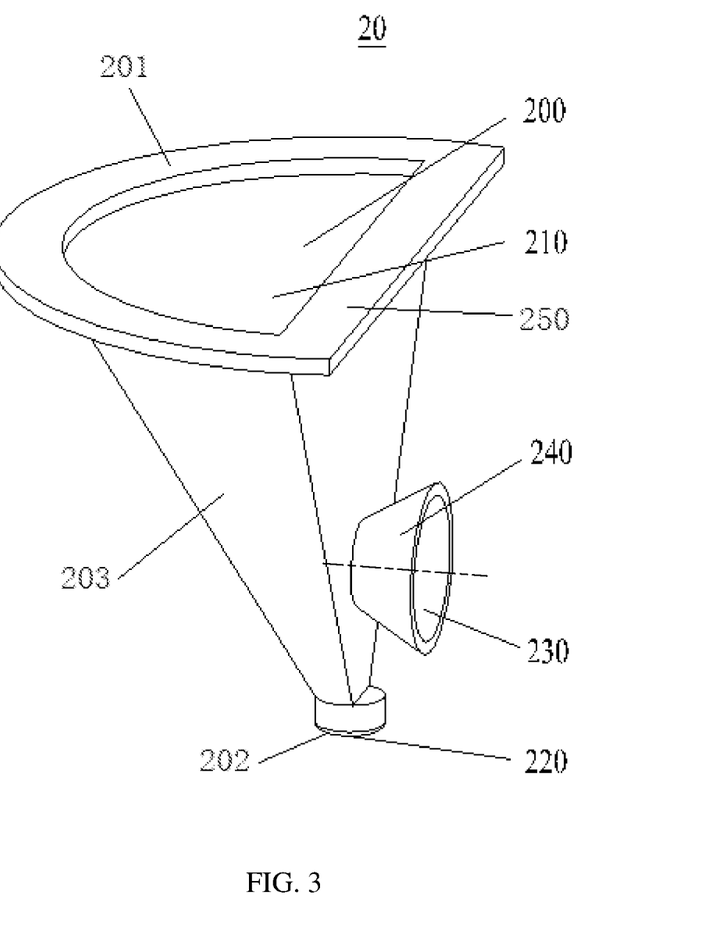
FIG. 3 is a schematic structural view of a collect part of the sample collecting device according to an embodiment of the disclosure.

The collect part 20 may be assembled into the accommodation chamber. A dumping opening 100 is provided on the left of the top plate, and the collecting port 210 may be located at the dumping opening 100. The collect part 20 may be assembled into the accommodation chamber from the dumping port 100, a periphery of the collecting port 210 may be surrounded by a limiting convex 250 protruding radially, and the limiting convex 250 can be clamped with a peripheral surface of the dumping port 100.

The sample collecting device 1 may include a water supply pipe 40 for supplying flushing water. The water supply pipe 40 is formed with a water supply channel having a water inlet and a water outlet 401, and the water inlet is connected with an external water source. The water supply pipe 40 is located on the top plate. The water outlet 401 is arranged opposite to the collecting port 210 in a vertical direction, so as to supply a water to flush an inner wall of the collecting cavity 200. The water supply pipe 40 is located above the collect part 20. The water supply pipe 40 may be assembled to the top plate.

The sample collecting device 1 may include a receiving box 50 for receiving the flushing water. The receiving box 50 is provided with a receiving tank with a receiving port. The receiving box 50 is located in the accommodation chamber. The receiving port is arranged opposite to the discharge outlet 220 in a vertical direction, so that the water flows into the receiving tank after flushing an inner wall of the collecting cavity 200. Then, the receiving box 50 is located under the collect part 20. The receiving box 50 may be assembled in the accommodation chamber. The receiving box may be drawer mounted. The receiving box 50 may be pulled out from the left side plate. The receiving box 50 may be provided with a handle 51.

The control part 30 is used for collecting samples. The control part 30 is configured to make the collecting rod put into the reagent bottle be pulled out of the reagent bottle and inserted into the collecting cavity 200 to collect samples, and configured to make the collecting rod with samples be pulled out from the collecting cavity 200 and put back into the reagent bottle. When the side wall 203 of the collecting cavity 200 is provided with the insertion port 230, the collecting rod is capable of be inserted into the collecting cavity 200 from the insertion port 230.

Figure 4:
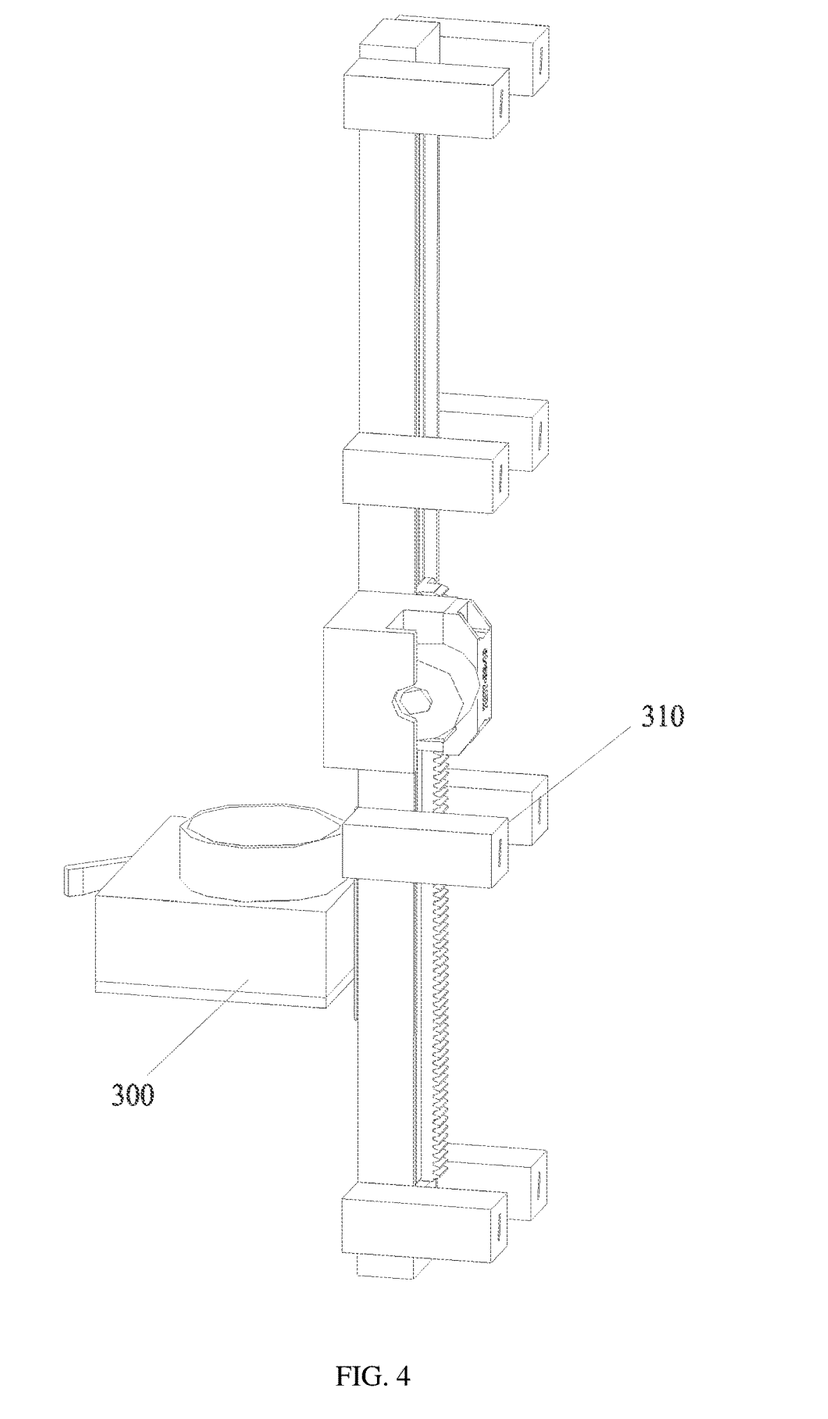
FIG. 4 is a schematic structural view of a vertical assembly of the sample collecting device according to an embodiment of the disclosure.
Figure 5:
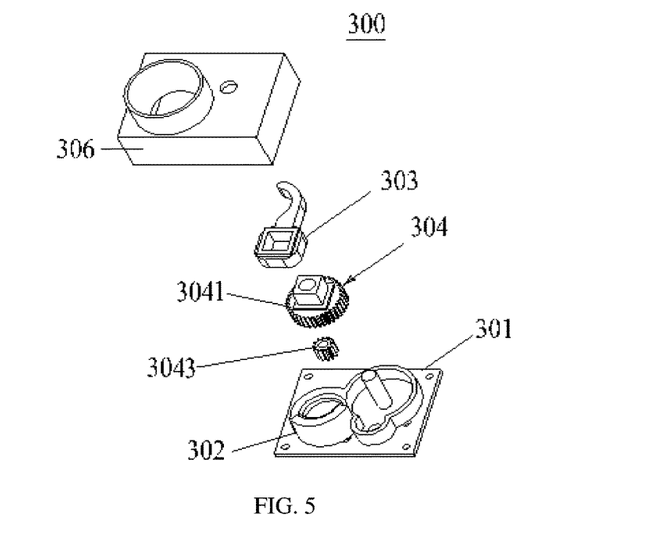
FIG. 5 is a schematic structural view of a first holder of the sample collecting device according to an embodiment of the disclosure.
Figure 7:
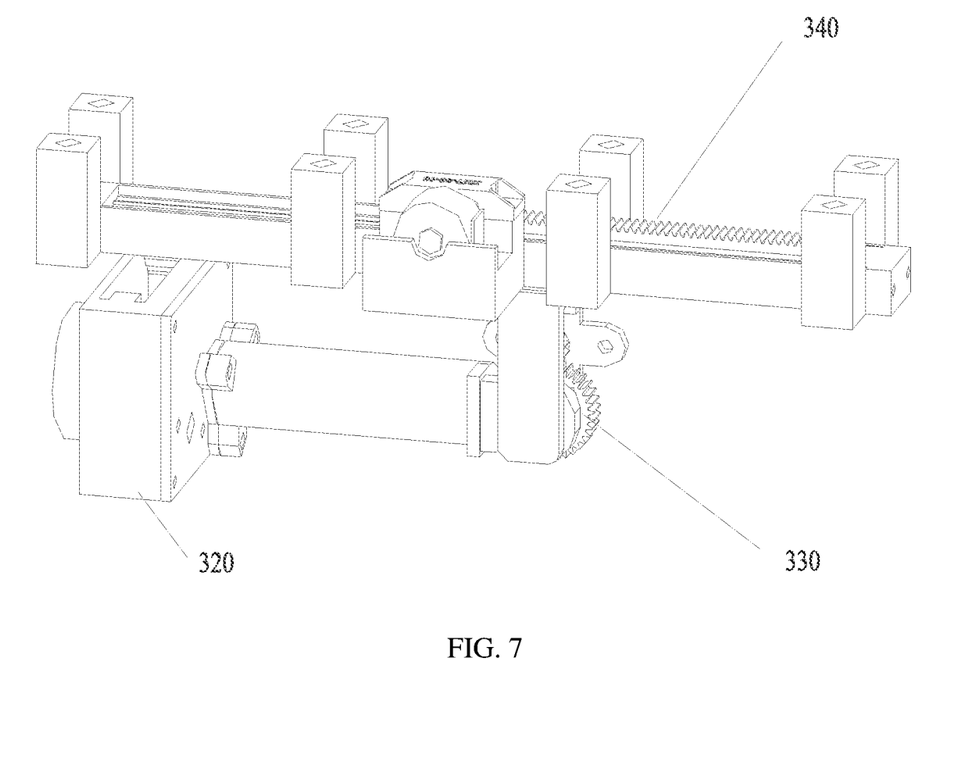
FIG. 7 is a schematic structural view of an upper assembly of the sample collecting device according to an embodiment of the disclosure.

The control part 30 may include a first holder 300, a first driver 310, a second holder 320, a rotator 330 and a second driver 340. The first holder 300 is used for fixing the reagent bottle with the collecting rod. The first holder 300 is configured to clamp and fix the reagent bottle in which the collecting rod is put, in a state of an opening of the reagent bottle being upward. The first holder 300 may include a first fixing seat 301, a first positioning piece 302, a first clamping member 303 and a first motor. The first fixing seat 301 is used for supporting the reagent bottle and the other parts of the first holder 300.

The first positioning piece 302 is used for limit the position of the reagent bottle. The first positioning piece 302 can be an arc-shaped strip. Then a peripheral wall of the reagent bottle can fit with a side wall of the first positioning piece 302 correspondingly. The first positioning piece 302 may be a convex disposed on an upper side of the first fixing seat 301.

The first clamping member 303 is used for clamping the reagent bottle in cooperation with the first positioning piece 302. The first clamping member 303 can be an arc-shaped strip. Then, the peripheral wall of the reagent bottle can fit with a side wall of the first clamping member 303 correspondingly. A first end of the first clamping member 303 can be connected with the first motor by a first gear set 304, so that the first clamping member 303 can be driven to rotate around its own axis by the first motor, and after rotating to a certain angle, it clamps the reagent bottle in cooperation with the first positioning piece 302. The first clamping member 303 may be assembled rotatably around its own axis on the upper side of the first fixing seat 301.

In order to achieve the above purpose, the following solutions can be adopted: the upper side of the first fixing seat 301 is provided with a first pillar, and the radial section of the outer wall of the first pillar is circular. A first fixing hole may be provided on the first end of the first clamping member 303; an axis of the first fixing hole may be parallel to the axis of the first clamping member 303, and a radial section of the inner wall of the first fixing hole is non-circular. The first gear set 304 includes a first power output gear 3043 and a first power input gear 3041. An axis of a central through hole of the first power output gear 3043 is parallel to the axis of the first clamping member 303, and a radial section of an inner wall of a central through hole of the first power output gear 3043 is non-circular. An axis of the first power input gear 3041 is parallel to the axis of the first clamping member 303, a radial section of an inner wall of a central through hole of the first power input gear 3041 is circular, and a periphery of the central through hole of the first power input gear 3041 is surrounded by a first fixing convex. A radial section of an outer wall of the first fixing convex is non-circular, and an outer diameter of the first power input gear 3041 is larger than that of the first power output gear 3043. An axis of the output shaft of the first motor is parallel to the axis of the first clamping member 303, and an output shaft of the first motor may be non-circular. The output shaft of the first motor is inserted into the central through hole of the first power output gear 3043 to drive the first power output gear 3043 to rotate. The first power output gear 3043 rotates and meshes with the first power input gear 3041 so as to drive the first power input gear 3041 rotate. The first pillar is inserted into the central through hole of the first power input gear 3041, and the first fixing convex is inserted into the first fixing hole to drive the first clamping member 303 to rotate.

The first motor may be assembled to a lower side of the first fixing seat 301, the upper side of the first fixing seat 301 is provided with a first mounting through hole, and the output shaft of the first motor is located on the upper side of the first fixing seat 301 through the first mounting through hole. The first holder includes a first cover 306, the first cover 306 is disposed above the first fixing seat 301 and covers the first fixing seat 301, and the first gear set 304 and the first clamping member 303 are disposed to a space limited by the first cover 306 and the first fixing seat 301, in order to prevent the first gear set 304 and the first clamping member 303 from falling off.

Figure 6:
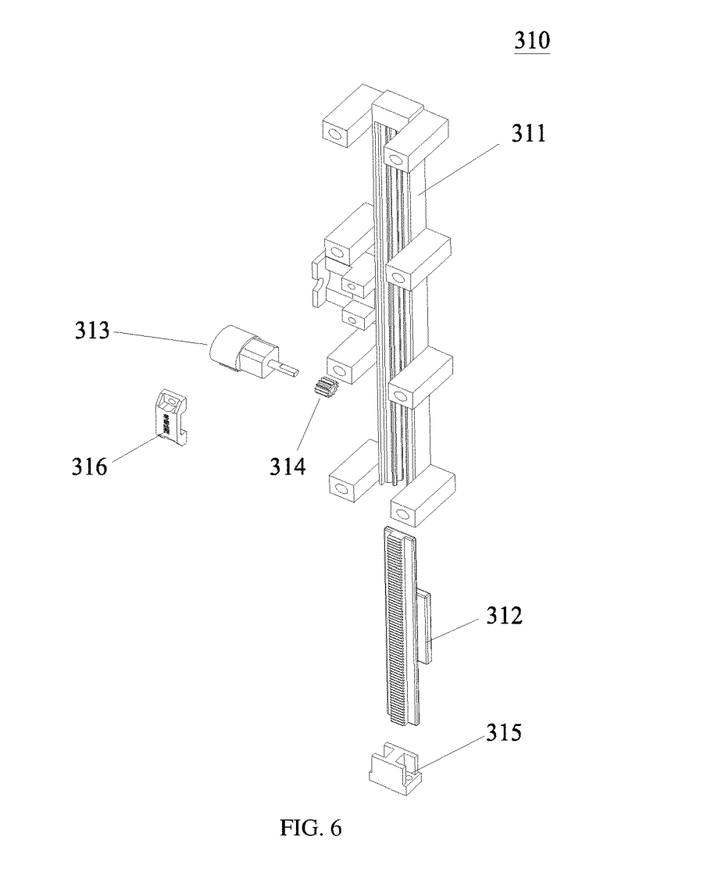
FIG. 6 is a schematic structural view of a first driver of the sample collecting device according to an embodiment of the disclosure.

The first driver 310 is used to drive the first holder 300. The first driver 310 is connected with the first holder 300. The first driver 310 may be configured to make the first holder 300 to move along the vertical direction. The first driver 310 may include a first bracket 311, a first rack 312, a first driving motor 313, and a first driving gear 314. The first bracket 311 is used to support the other parts of the first driver 310. The first bracket 311 may be provided with a first strip opening extending in a vertical direction. A first end of the first strip opening can be opened.

The first rack 312 is used for connecting with the first holder 300 and transmitting power. The first rack 312 is disposed in the vertical direction. The back of the first rack 312 is provided with a slide rail, which is vertically arranged, and the slide rail is slidably assembled into the first strip opening, and a side of the slide rail away from the first rack 312 is connected with the first holder 300. The slide rail can slide into the first strip opening from the first end of the first strip opening.

The first rack 312 is connected with the first driving motor 313 by the first driving gear 314, so that the first rack 312 is driven to move along the vertical direction by the first driving motor 313, and thereby drives the first holder 300 to move in the vertical direction together. Then, an axis of the first driving gear 314 extends horizontally, and a radial section of an inner wall of a central through hole of the first driving gear 314 is non-circular. An axis of the output shaft of the first driving motor 313 is horizontally extended, and a radial section of an outer wall of the output shaft of the first driving motor 313 is non-circular, so that the output shaft of the first driving motor 313 is inserted into the central through hole of the first driving gear 314 to drive the first driving gear 314 to rotate, then drives the first rack 312 meshed with the first driving gear 314 to move in the vertical direction.

The first driver 310 includes a first plugging piece 315. The first plugging piece 315 plugs the first end of the first bracket 311. The first driver 310 may include a first mounting piece 316. The first driving motor 313 is assembled to the first bracket 311 through the first mounting piece 316 in cooperation with a plurality of bolts.

The second holder 320 is used for fixing the collecting rod. The second holder 320 is located above the first holder 300. The second holder 320 can be configured to clamp and fix the collecting rod put into the reagent bottle. The second holder 320 may include a second fixing seat, a second positioning piece, a second clamping member and a second motor. The second fixing seat is used for supporting the other parts of the second holder 320.

The second positioning piece is used for positioning the collecting rod. The second positioning piece can be an arc-shaped strip. Then, the peripheral wall of the collecting rod can fit with the side wall of the second positioning piece. The second positioning piece may be a convex on the upper side of the second fixing seat.

The second clamping member is used for clamping the collecting rod in cooperation with the second positioning piece. The second clamping member can be an arc-shaped strip. Then, the peripheral wall of the collecting rod can fit with the side wall of the second clamping member correspondingly. A second end of the second clamping member can be connected with the second motor by a second gear set, so that the second clamping member may be driven to rotate around its own axis by the second motor, and after rotating to a certain angle, it can clamp and fix the collecting rod in cooperation with the second positioning piece. The second clamping member may be assembled rotatably around its own axis on the upper side of the second fixing seat.

In order to achieve the above purpose, the following solutions can be adopted: the upper side of the second fixing seat is provided with a second pillar, and the radial section of the outer wall of the second pillar is circular. A second fixing hole is provided on the second end of the second clamping member, an axis of the second fixing hole can be parallel to an axis of the second clamping member, and a radial section of an inner wall of the second fixing hole is non-circular. The second gear set includes a second power output gear and a second power input gear. An axis of a central through hole of the second power output gear is parallel to the axis of the second clamping member, and a radial section of an inner wall of the central through hole of the second power output gear is non-circular. An axis of the second power input gear is parallel to the axis of the second clamping member, a radial section of an inner wall of the central through hole of the second power input gear is circular, and a periphery of the central through hole of the second power input gear is surrounded by a second fixing convex. A radial section of an outer wall of the second fixing convex is non-circular, and an outer diameter of the second power input gear is larger than that of the second power output gear. An axis of the output shaft of the second motor is parallel to the axis of the second clamping member, and the output shaft of the second motor can be non-circular. The output shaft of the second motor is inserted into the central through hole of the second power output gear to drive the second power output gear to rotate. The second power output gear rotates and meshes with the second power input gear to drive the second power input gear to rotate. The second pillar is inserted into the central through hole of the second power input gear, and the second fixing protrusion is inserted into the second fixing hole to drive the second clamping member to rotate.

The second motor can be assembled to the lower side of the second fixing seat, the upper side of the second fixing seat can be provided with a second mounting through hole, and the output shaft of the second motor can be located on the upper side of the second fixing seat through the second mounting through hole. The second holder can include a second cover body, the second cover body cover is disposed above the second fixing seat, and the second gear set, the second clamping member and so on are arranged in a space limited by the second cover body and the second fixing seat, so as to prevent the second gear set, the second clamping member and so on from falling off. It should be noted that, the second holder is upside down during installation in order to ensure that the second holder 320 can clamp and fix the collecting rod put into the reagent bottle.

The rotator 330 is used for rotating the second holder 320. The rotator 330 is connected with the second holder 320. The second holder 320 can be configured to make the second holder 320 rotate to ensure the axis of the collecting rod fixed by the second holder 320 coincides with the axis of the insertion port 230, and to make the collecting rod fixed by the second holder 320 vertically set. The rotator 330 may include a base, a connecting piece and a rotating motor, the connecting piece and the rotating motor are respectively installed on the base, the connecting piece is connected with the rotating motor through a rotating gear set, the connecting piece is connected with the second holder 320, and the base is connected with the second driver 340, so that the connecting piece is driven to rotate by the rotating motor and drives the second holder 320 to rotate.

In order to achieve the above purpose, the following solutions can be adopted: an upper side of the base is provided with a rotating pillar, and a radial section of an outer wall of the rotating pillar is circular. A first end of the connecting piece can be provided with a connecting hole, and a radial section of an inner wall of the connecting hole is non-circular. The rotating gear set includes a first connecting gear and a second connecting gear. An axis of a central through hole of the first connecting gear is parallel to that of the connecting hole, and a radial section of the inner wall of the central through hole of the first connecting gear is non-circular. An axis of the second connecting gear coincides with the axis of the connecting hole, a radial section of an inner wall of the central through hole of the second connecting gear is circular, and a periphery of the central through hole of the second connecting gear is surrounded by a connecting convex. A radial section of an outer wall of the connecting convex is non-circular, and an outer diameter of the second connecting gear is larger than that of the first connecting gear. An axis of an output shaft of the rotating motor is parallel to the axis of the connecting hole, and the output shaft of the rotating motor can be non-circular. The output shaft of the rotating motor is inserted into the central through hole of the first connecting gear to drive the first connecting gear to rotate. The first connecting gear rotates and meshes with the second connecting gear to drive the second connecting gear rotate. The rotating pillar is inserted into the central through hole of the second connecting gear, and the connecting convex is inserted into the connecting hole to drive the connecting piece to rotate.

It should be noted that the rotator 330 is installed on a side to ensure that the axis of the collecting rod fixed by the second holder 320 can coincide with the axis of the insertion port 230 and be set vertically. The rotator 330 may include a positioning frame. The positioning frame is connected with a top end of the rotating pillar and the base, so as to prevent the rotating gear set and the connecting piece from the falling off.

The second driver 340 is used to drive the second holder. The second driver 340 is connected with the rotator 330. The second driver 340 may be configured to make the second holder move along the axial direction (as denoted by the dashed line in FIG. 3) of the insertion port. The second driver 340 may include a second bracket, a second rack and a second driving motor. The second bracket is used for supporting the other parts of the second driver 340. The second bracket may be provided with a second strip opening extending along the axial direction of the insertion opening. A second end of the second strip opening can be opened.

The second rack is used for connecting with the second holder and transmitting power. The second rack is arranged along the axial direction (as denoted by the dashed line in FIG. 3) of the insertion port. The back of the second rack can be provided with a slide rail, the slide rail is axially arranged in the axial direction of insertion port, the slide rail is slidably assembled into the second strip opening, and a side of the slide rail away from the second rack is connected with the second holder. The slide rail can slide into the second strip opening from the second end of the second strip opening.

The second rack is connected with the second driving motor through the second driving gear, so that the second rack is driven to move in the axial direction (as denoted by the dashed line in FIG. 3) of the insertion port by the second driving motor, and thereby drives the second holder to move in the axial direction of the insertion port. Then, the axis of the second driving gear extends horizontally, and a radial section of an inner wall of the central through hole of the second driving gear is non-circular. An axis of an output shaft of the second driving motor extends horizontally, and a radial section of an outer wall of the output shaft of the second driving motor is non-circular, so that the output shaft of the second driving motor is inserted into the central through hole of the second driving gear to drive the second driving gear to rotate, so as to drive the second rack meshed with the second driving gear to move in the axial direction of the insertion port.

The second driver 340 may include a second plugging piece. The second plugging piece plugs the second end of the second bracket. The second driver 340 may include a second mounting piece. The second driving motor is assembled to the second bracket through the second mounting piece in cooperation with a plurality of bolts.

The first holder 300, the first driver 310, the second holder 320, the rotator 330 and the second driver 340 can be assembled in the accommodation chamber. The front plate may be provided with an operating port 110, and the first holder 300 is located at the operating port 110. The front plate may be provided with an observation port 120, and the collect part 20 is located at the observation port 120. The two opposite sides of the first driver 310 can be respectively provided with a plurality of first connecting pillars, and the first connecting pillar is provided with a first fixing hole, so that the first driver 310 can be installed on the right side plate in cooperation with bolts. The two opposite sides of the second driver 340 can be respectively provided with a plurality of second connecting pillars, and the second connecting pillar is provided with a second fixing hole, so that the second driver 340 can be installed on the right side of the top plate in cooperation with bolts. The first holder 300 and the first driver 310 can be integrated as a whole, which is called as a vertical assembly. The second holder 320, the rotator 330 and the second driver 340 can be integrated as a whole, which is called as the upper assembly.

In the working process of the sample collecting device 1, firstly, the reagent bottle inserted with the collecting rod is placed in the vertical assembly manually or by manipulator, and clamped in the vertical integration. The reagent bottle with the collecting rod is driven to move upward by the vertical manually, until the collecting rod enters the upper assembly. After the collecting rod is clamped by the upper assembly, the reagent bottle is driven to move downward by the vertical assembly to separate the reagent bottle from the collecting rod. Then the collecting rod is driven by the upper integration to rotate so that the collecting rod is aligned with the insertion port 230. Then, the collecting rod is driven by the upper integration to move horizontally and is inserted into the insertion port 230 for collecting sample. After the collection, the collecting rod is driven by the upper assembly to move in reverse. Then the collecting rod is driven to rotate so that the collecting rod is aligned with the reagent bottle. Then the reagent bottle is driven by the vertical assembly to move upward so that the collecting rod is inserted into the reagent bottle. After the upper assembly releases the collecting rod, the reagent bottle inserted with the collecting rod is driven by the vertical assembly to move downward to a designated position, and finally the vertical assembly releases the reagent bottle inserted with the collecting rod to complete the sample collection.

The disclosure realizes the sample collecting without manual intervention, ensures the effectiveness and consistency of the collected samples, and reduces labor cost.

The control part 30 may further include an electric control box 350. The electric control box 350 is connected with the first motor, the first driving motor, the second motor, the rotating motor and the second driving motor. The electric control box 350 is configured to control the operation of the first motor, the first driving motor, the second motor, the rotating motor and the second driving motor. The electric control box 350 can be assembled on the rear plate. The control part 30 may include a plurality of position sensors configured to detect the positions and states of the first holder 300 and the second holder 320. The position sensor can be a photoelectric sensor. The electronic control box 350 can be connected with each position sensor to control according to the positions and states of the collecting rod and the reagent bottle. The control part 30 may further include a plurality of position limiting structures configured to limit the positions of the first holder 300 and the second holder 320.

The same or similar labels in the drawings of the embodiments correspond to the same or similar components; in the description of this disclosure, it should be understood that if the orientation or position relationship indicated by the terms "up", "down", "left", "right" is based on the orientation or position relationship shown in the drawings, it is only for the convenience of describing this disclosure and simplifying the description, rather than indicating or implying that the device or element of the invention must have a specific orientation, be constructed and operated in a specific orientation. Therefore, the terms describing the positional relationship in the drawings are only for illustrative purposes and cannot be understood as limiting the disclosure. For those of ordinary skill in the art, the specific meaning of the above terms can be understood according to the specific situation.

The above is only a better embodiment of the disclosure and does not limit the disclosure. Any modification, equivalent substitution and improvement made within the spirit and principles of the disclosure shall be included in the protection scope of the disclosure.

What is claimed is:
1. A sample collecting device, operative with a collecting rod and a reagent bottle, the sample collecting device comprising:
   a frame;
   a collect part, disposed in the frame, wherein the collect part is provided with a collecting cavity having a collecting port, and the collect part is configured to make a sample flow into the collecting cavity from the collecting port; and a control part, disposed in the frame, wherein the control part is configured to make the collecting rod put into the reagent bottle be pulled out of the reagent bottle and inserted into the collecting cavity to collect the sample, and configured to make the collecting rod with the sample be pulled out from the collecting cavity and put back into the reagent bottle;

wherein the collecting port is located on a top wall of the collecting cavity, a discharge outlet is provided on a bottom wall of the collecting cavity, and an insertion port is provided on a side wall of the collecting cavity, so that the sample is capable of flowing into the collecting cavity from the collecting port and then discharging from the discharge outlet, and the collecting rod is capable of being inserted into the collecting cavity from the insertion port;

wherein the control part comprises:

a first holder, configured to clamp and fix the reagent bottle, in which the collecting rod is put, in a state of an opening of the reagent bottle being upward;

a first driver, connected with the first holder, wherein the first driver is configured to drive the first holder to move in a vertical direction;

a second holder, disposed above the first holder, wherein the second holder is configured to clamp and fix the collecting rod put into the reagent bottle;

a rotator, connected with the second holder, wherein the rotator is configured to rotate the second holder to make an axis of the collecting rod fixed by the second holder coincide with an axis of the insertion port and the collecting rod fixed by the second holder be vertically arranged; and a second driver, connected with the rotator, wherein the second driver is configured to drive the rotator to move along an axial direction of the insertion port;

wherein the first holder comprises a first fixing seat, a first positioning piece, a first clamping member and a first motor; the first positioning piece, the first clamping member and the first motor are individually disposed on the first fixing seat, the first clamping member is connected with the first motor by a first gear set and thereby the first clamping member rotates under the driving of the first motor and then cooperates with the first positioning piece to clamp the reagent bottle; and wherein the second holder comprises a second fixing seat, a second positioning piece, a second clamping member and a second motor; the second positioning piece, the second clamping member and the second motor are individually disposed on the second fixing seat, the second clamping member is connected with the second motor by a second gear set and thereby the second clamping member rotates under the driving of the second motor and then cooperates with the second positioning piece to clamp the collecting rod.

2. The sample collecting device as claimed in claim 1, wherein the side wall of the collecting cavity is gradually tapered downward, so that the sample flowing in from the collecting port converges towards and discharges from the discharge outlet.

3. The sample collecting device as claimed in claim 1, wherein a periphery of the insertion port is surrounded by a guide wall outwardly protruding from the collecting cavity, and a side wall of the guide wall gradually expands along a direction away from the collecting cavity, so that the collecting rod is capable of being inserted into the collecting cavity from the insertion port under the guiding of the guide wall.

4. The sample collecting device as claimed in claim 1, further comprising:

a water supply pipe, wherein the water supply pipe is disposed on the frame, the water supply pipe is formed with a water supply channel having a water inlet and a water outlet, the water inlet is connected with an external water source, and the water outlet is arranged opposite to the collecting port in a vertical direction so as to supply a water to flush an inner wall of the collecting cavity.

5. The sample collecting device as claimed in claim 1, further comprising:

a receiving box, wherein the receiving box is disposed in the frame, the receiving box is provided with a receiving tank having a receiving port, and the receiving port is arranged opposite to the discharge outlet in a vertical direction so as to a water flows into the receiving tank after flushing an inner wall of the collecting cavity.

6. The sample collecting device as claimed in claim 1, wherein the first driver comprises a first bracket, a first rack, a first driving motor and a first driving gear; the first rack, the first driving gear and the first driving motor are individually disposed on the first bracket; the first rack is arranged along the vertical direction, the first rack is connected with the first driving motor through the first gear set, the first rack is connected with the first holder, so that the first rack is driven to move in the vertical direction by the first driving motor and thereby drives the first holder to move in the vertical direction;

wherein the second driver comprises a second bracket, a second rack, a second driving motor and a second driving gear; the second rack, the second driving gear and the second driving motor are individually disposed on the second bracket; the second rack is arranged along the axial direction of the insertion port, the second rack is connected with the second driving motor through the second driving gear, and the second rack is connected with the rotator, so that the second rack is driven to move along the axial direction of the insertion port by the second driving motor and thereby drives the rotator to move in the axial direction of the insertion port.

7. The sample collecting device as claimed in claim 1, wherein the rotator comprises a base, a connecting piece and a rotating motor; the connecting piece and the rotating motor are individually disposed on the base, the connecting piece is connected with the rotating motor through a rotating gear set, the connecting piece is connected with the second holder, and the base is connected with the second driver, so that the connecting piece is driven to rotate by the rotating motor and thereby drives the second holder to rotate.

8. A sample collecting device, operative with a collecting rode and a reagent bottle, the sample collecting device comprising:

a frame;

a collect part, disposed in the frame, wherein the collect part is provided with a collecting cavity having a collecting port, and the collect part is configured to make a sample flow into the collecting cavity from the collecting port; and a control part, disposed in the frame, wherein the control part is configured to make the collecting rod put into the reagent bottle be pulled out of the reagent bottle and inserted into the collecting cavity to collect the sample, and configured to make the collecting rod with the sample be pulled out from the collecting cavity and put back into the reagent bottle;

wherein the collecting port is located on a top wall of the collecting cavity, a discharge outlet is provided on a bottom wall of the collecting cavity, and an insertion port is provided on a side wall of the collecting cavity, so that the sample is capable of flowing into the collecting cavity from the collecting port and then discharging from the discharge outlet, and the collecting rod is capable of being inserted into the collecting cavity from the insertion port;

wherein the control part comprises:
- a first holder, configured to clamp and fix the reagent bottle, in which the collecting rod is put, in a state of an opening of the reagent bottle being upward;
- a first driver, connected with the first holder, wherein the first driver is configured to drive the first holder to move in a vertical direction;
- a second holder, disposed above the first holder, wherein the second holder is configured to clamp and fix the collecting rod put into the reagent bottle;
- a rotator, connected with the second holder, wherein the rotator is configured to rotate the second holder to make an axis of the collecting rod fixed by the second holder coincide with an axis of the insertion port and the collecting rod fixed by the second holder be vertically arranged; and
- a second driver, connected with the rotator, wherein the second driver is configured to drive the rotator to move along an axial direction of the insertion port;

wherein the first driver comprises a first bracket, a first rack, a first driving motor and a first driving gear; the first rack, the first driving gear and the first driving motor are individually disposed on the first bracket; the first rack is arranged along the vertical direction, the first rack is connected with the first driving motor through the first gear set, the first rack is connected with the first holder, so that the first rack is driven to move in the vertical direction by the first driving motor and thereby drives the first holder to move in the vertical direction; and wherein the second driver comprises a second bracket, a second rack, a second driving motor and a second driving gear; the second rack, the second driving gear and the second driving motor are individually disposed on the second bracket; the second rack is arranged along the axial direction of the insertion port, the second rack is connected with the second driving motor through the second driving gear, and the second rack is connected with the rotator, so that the second rack is driven to move along the axial direction of the insertion port by the second driving motor and thereby drives the rotator to move in the axial direction of the insertion port.

9. A sample collecting device, operative with a collecting rode and a reagent bottle, the sample collecting device comprising:
- a frame;
- a collect part, disposed in the frame, wherein the collect part is provided with a collecting cavity having a collecting port, and the collect part is configured to make a sample flow into the collecting cavity from the collecting port; and
- a control part, disposed in the frame, wherein the control part is configured to make the collecting rod put into the reagent bottle be pulled out of the reagent bottle and inserted into the collecting cavity to collect the sample, and configured to make the collecting rod with the sample be pulled out from the collecting cavity and put back into the reagent bottle;

wherein the collecting port is located on a top wall of the collecting cavity, a discharge outlet is provided on a bottom wall of the collecting cavity, and an insertion port is provided on a side wall of the collecting cavity, so that the sample is capable of flowing into the collecting cavity from the collecting port and then discharging from the discharge outlet, and the collecting rod is capable of being inserted into the collecting cavity from the insertion port;

wherein the control part comprises:
- a first holder, configured to clamp and fix the reagent bottle, in which the collecting rod is put, in a state of an opening of the reagent bottle being upward;
- a first driver, connected with the first holder, wherein the first driver is configured to drive the first holder to move in a vertical direction;
- a second holder, disposed above the first holder, wherein the second holder is configured to clamp and fix the collecting rod put into the reagent bottle;
- a rotator, connected with the second holder, wherein the rotator is configured to rotate the second holder to make an axis of the collecting rod fixed by the second holder coincide with an axis of the insertion port and the collecting rod fixed by the second holder be vertically arranged; and
- a second driver, connected with the rotator, wherein the second driver is configured to drive the rotator to move along an axial direction of the insertion port; and wherein the rotator comprises a base, a connecting piece and a rotating motor; the connecting piece and the rotating motor are individually disposed on the base, the connecting piece is connected with the rotating motor through a rotating gear set, the connecting piece is connected with the second holder, and the base is connected with the second driver, so that the connecting piece is driven to rotate by the rotating motor and thereby drives the second holder to rotate.

\* \* \* \* \*